United States Patent
Le Scouarnec et al.

(10) Patent No.: US 10,027,347 B2
(45) Date of Patent: Jul. 17, 2018

(54) METHODS FOR STORING AND READING DIGITAL DATA ON A SET OF DNA STRANDS

(71) Applicant: THOMSON LICENSING, Issy les Moulineaux (FR)

(72) Inventors: Nicolas Le Scouarnec, Liffre (FR); Jean Bolot, Los Altos, CA (US); Brian Eriksson, San Jose, CA (US); Sebastien Lasserre, Thorigné Fouillard (FR); Mark Crovella, Wayland, MA (US); Meinolf Bilawat, Hannover (DE); Klaus Gaedke, Hannover (DE); Jens Peter Wittenburg, Isernhagen (DE); Christophe Diot, Paris (FR); Martin May, Cesson-Sevigne (FR)

(73) Assignee: THOMSON Licensing, Issy-les-Moulineaux (FR)

(*) Notice: Subject to any disclaimer, the term of this patent is extended or adjusted under 35 U.S.C. 154(b) by 0 days.

(21) Appl. No.: 15/300,269

(22) PCT Filed: Mar. 26, 2015

(86) PCT No.: PCT/EP2015/056660
§ 371 (c)(1),
(2) Date: Sep. 28, 2016

(87) PCT Pub. No.: WO2015/144858
PCT Pub. Date: Oct. 1, 2015

(65) Prior Publication Data
US 2017/0187390 A1 Jun. 29, 2017

(30) Foreign Application Priority Data
Mar. 28, 2014 (EP) .................................. 14305460

(51) Int. Cl.
*H03M 13/00* (2006.01)
*H03M 13/09* (2006.01)
(Continued)

(52) U.S. Cl.
CPC .......... *H03M 13/09* (2013.01); *C12Q 1/6806* (2013.01); *G06F 3/064* (2013.01); *G06F 3/065* (2013.01);
(Continued)

(58) Field of Classification Search
CPC ............. H03M 13/09; H03M 13/1102; H03M 13/1515; H03M 13/154; H03M 13/2906;
(Continued)

(56) References Cited

U.S. PATENT DOCUMENTS

| 2004/0001371 A1* | 1/2004 | Mansuripur | B82Y 10/00 365/200 |
| 2007/0113137 A1* | 5/2007 | Ryu | H03M 13/15 714/746 |
| 2008/0065951 A1* | 3/2008 | Takagi | G11B 20/1803 714/755 |

FOREIGN PATENT DOCUMENTS

| EP | 1512749 | 3/2005 |
| WO | WO2013178801 | 12/2012 |

OTHER PUBLICATIONS

Tulpan et al., "HyDEn: A Hybrid Steganocryptographic Approach for Data Encryption Using Randomized Error-Correcting DNA Codes", Biomed Research International, vol. 2013, Article No. 634832, 2013, pp. 1-12.
(Continued)

*Primary Examiner* — Sam Rizk
(74) *Attorney, Agent, or Firm* — Brian J. Dorini; Jeffrey M. Navon

(57) ABSTRACT

In one embodiment, it is proposed a method for storing input data on a set of DNA strands, said input data being repre-
(Continued)

sented in a numeral system. This method is remarkable in that it comprises: formatting said input data into a set of blocks of data, each block of data having a size inferior to a size of one DNA strand; applying a first encoding with an erasure code on said set of blocks of data, defining a first set of modified blocks of data, each modified block of data having a size inferior to a size of one DNA strand; applying a second encoding using an error correcting code on each modified block of data of said first set, defining a second set of modified blocks of data, each modified block having a size inferior to a size of one DNA strand; encoding each modified block of data of said second set into a nucleotides block sequence; generating a set of DNA strands, each DNA strand comprising a nucleotides block sequence obtained through said encoding.

16 Claims, 5 Drawing Sheets

(51) Int. Cl.
| | | |
|---|---|---|
| *G06F 3/06* | (2006.01) | |
| *G06F 11/10* | (2006.01) | |
| *H03M 13/11* | (2006.01) | |
| *H03M 13/15* | (2006.01) | |
| *H03M 13/29* | (2006.01) | |
| *G06F 19/28* | (2011.01) | |
| *C12Q 1/6806* | (2018.01) | |

(52) U.S. Cl.
CPC .......... *G06F 3/0619* (2013.01); *G06F 3/0661* (2013.01); *G06F 3/0673* (2013.01); *G06F 11/1004* (2013.01); *G06F 11/1076* (2013.01); *G06F 19/28* (2013.01); *H03M 13/1102* (2013.01); *H03M 13/154* (2013.01); *H03M 13/1515* (2013.01); *H03M 13/2906* (2013.01); *H03M 13/6502* (2013.01)

(58) Field of Classification Search
CPC .. H03M 13/6502; G06F 3/0619; G06F 3/064; G06F 3/065; G06F 3/0661; G06F 3/0673; G06F 11/1004; G06F 11/1076
See application file for complete search history.

(56) References Cited

OTHER PUBLICATIONS

Bystrykh, "Generalized DNA Barcode Design Based on Hamming Codes", PLOS ONE, vol. 7, No. 5, May 2012, pp. 1-8.
Buschmann et al., "Levenshtein error-correcting barcodes for multiplexed DNA sequencing", BMC Bioinformatics, vol. 14, No. 11, Jan. 2013, pp. 272-281.
Byers et al., "A Digital Fountain Approach to Asynchronous Reliable Multicast", IEEE Journal on Selected Areas in Communications, Special Issue on Network Support for Multicast Communication, vol. 20, No. 8, Oct. 2002, pp. 1528-1540.
Church et al., "Next-Generatio Digital Information Storage in DNA", Science, vol. 337, Sep. 28, 2012, p. 1628.

\* cited by examiner

METHODS FOR STORING AND READING DIGITAL DATA ON A SET OF DNA STRANDS

This application claims the benefit, under 35 U.S.C. § 365 of International Application PCT/EP2015/056660, filed Mar. 26, 2015, which was published in accordance with PCT Article 21(2) on Oct. 1, 2015, in English, and which claims the benefit of European patent application No. 14305460.9, filed Mar. 28, 2014.

TECHNICAL FIELD

The invention relates to a technique for storing digital data over DNA (acronym which stands for Deoxyribonucleic Acid).

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

DNA storage techniques, as for example the one depicted in the document WO2013/178801 or in the article entitled *"Next Generation Digital Information Storage in DNA"* by G. M. Church et al., published in Science, 337:1628, 2012, rely on processes that have been developed for biology. Generally, the overall process consist in the five following steps: (i) encoding data to nucleotide sequences, (ii) writing data to DNA strands by synthesis (the synthesis process consist in printing. Its main characteristics are that it is relatively costly, and that it has a non-negligible error-rate), (iii) replicating DNA strands using a biochemical reaction (such as the PCRA, which stands for plasmid copy reduced; the PCRA is a relatively inexpensive bio-chemical reaction that produces many replicates of sequences that begin by a given primer. This allows selecting a subset of strands. This replication offers a protection against the alteration of a given strand, yet it just replicates error that happened before (e.g. during the synthesis), (iv) reading DNA strands by sequencing (the sequencing consists in picking randomly strands in a solution and reading their nucleotides (nucleotide by nucleotide). The error-rate per nucleotide is rather high) and (v) decoding the sequences of nucleotides to recover the data.

In order to avoid the loss of information, the technique of document WO2013/178801 uses an overlapping technique of DNA segments that create a kind of redundancy. The FIG. 2 of document WO2013/178801 presents a plurality of overlapping DNA segments that can ease the recovering of information during the sequencing. Indeed, it is necessary to use a protection against the loss of information due to the fact that there is a relatively high level of error during the steps of synthesis and sequencing.

The proposed technique proposes an alternative to the technique of document WO2013/178801 that can make the reading process much more efficient. The proposed technique also avoids using overlapping technique, and/or consensus technique.

SUMMARY OF THE DISCLOSURE

References in the specification to "one embodiment", "an embodiment", "an example embodiment", indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention is directed to a method for storing input data on a set of DNA strands, said input data being represented in a numeral system. This method is remarkable in that it comprises:

formatting said input data into a set of blocks of data, each block of data having a size inferior to a size of one DNA strand;

applying a first encoding with an erasure code on said set of blocks of data, defining a first set of modified blocks of data, each modified block of data having a size inferior to a size of one DNA strand;

applying a second encoding using an error correcting code on each modified block of data of said first set, defining a second set of modified blocks of data, each modified block having a size inferior to a size of one DNA strand;

encoding each modified block of data of said second set into a nucleotides block sequence;

generating a set of DNA strands, each DNA strand comprising a nucleotides block sequence obtained through said encoding.

Hence, when storing digital data, the synthesized sequences are not constrained as they won't be "biologically" interpreted thus freeing us from purely replication-based schemes. This strongly departs from existing schemes (including the ones using codes mentioned as background (e.g., Church et al.)) for storing data onto DNA, and can lower sequencing (i.e., reading) costs by orders of magnitude. The two key aspects are the additional layer of protection beyond the modulation, that can provide a higher potential for correcting errors on strands, and the outer (fountain) code that allows to solve the coupon collector linked with random access to strands during sequencing. Existing schemes, even if designed for storing data onto DNA, have continued to rely on comparing multiple reads of a given strands and applying "consensus" to mitigate errors.

In a preferred embodiment, such method for storing is remarkable in that said generating uses a synthesis process.

In a preferred embodiment, such method for storing is remarkable in that said input data corresponds to data that has been obtained via a compression process. Since the tolerance to errors is enhanced, it becomes possible to store compressed data, which is more fragile as the decoder can amplify the errors. By compressing data prior to encoding and storing onto DNA, the amount of DNA to synthesize can be significantly reduced.

In a preferred embodiment, such method for storing is remarkable in that it further comprises replicating at least one strand that belongs to said set of DNA strands.

In a preferred embodiment, such method for storing is remarkable in that said numeral system corresponds to a binary numeral system. In a preferred embodiment, such method for storing is remarkable in that said encoding uses a look-up table that put into correspondence a sequence of elements of said numeral system into a sequence of nucleotides.

In a preferred embodiment, such method for storing is remarkable in that said encoding uses a modulation code or a convolutional code.

By using an appropriate modulation code such as a convolutional code, it becomes possible at demodulation to correct some local errors, or provide the LDPC with probabilities for the values of bits. The LDPC can then be soft-decoded. Also, the inner code and the modulation code can be jointly decoded allowing the correction of more errors and the exploitation all the information available. Also, a convolutional code can resynchronize the strands in case insertion/deletion of nucleotide is detected so as to cope with these kinds of errors.

In a preferred embodiment, such method for storing is remarkable in that it further comprises replicating DNA strands belonging to said generated set of DNA strands via a biochemical reaction.

In a preferred embodiment, such method for storing is remarkable in that said erasure code belongs to a group comprising:
- a fountain code;
- a tornado code;
- a low-density parity-check code;
- a Reed-Solomon code;
- a maximum distance separable code.

Codes such as fountain codes (e.g., LT or Raptor codes), tornado codes, LDPC codes have a low decoding complexity with good erasure correction properties for large enough code length which is interesting when a large number of strands is used/large amount of redundancy is synthesized. For smaller number of strands optimal codes such as Reed-Solomon codes or any other maximum distance separable codes can be used.

In a preferred embodiment, such method for storing is remarkable in that said error correcting code belongs to a group comprising:
- a low-density parity-check code;
- a Reed-Solomon code.

Codes such as LDPC are interesting for long strands (large number of nucleotide) thanks to their low decoding complexity and their good error correction properties for large code length. For shorter strands, optimal codes such as Reed-Solomon or any other Maximum Distance Separable Codes can be used.

In a preferred embodiment, such method for storing according is remarkable in that it further comprises applying a cyclic redundancy check code either on said first set or on said second set.

The CRC allows to lower the probability that the outer decoder is fed with an erroneous "strand" yet remain optional since the inner code should already identify that it can't decode and only exceptional circumstances would lead to the inner code being decoded erroneously.

In a preferred embodiment, such method for storing is remarkable in that said generating a set of DNA strands further comprises inserting a common primer on said generated DNA strands.

Adding primers to the generated DNA strands allows selecting a subset of strands to sequence using PCRA, and also allows bootstrapping the bio-chemical replication process.

In a variant, it is proposed a method for obtaining useful data via a set of DNA strands. This method is remarkable in that it comprises:
- selecting at random DNA strands belonging to said set of DNA strands;
- sequencing said selected DNA strands, delivering a set of nucleotides block sequence;
- converting each nucleotides block sequence into a numeral system, each nucleotides block sequence being associated with a corresponding block of data;
- applying a first decoding using an error correcting code on each block of data, defining a first set of decoded blocks of data;
- applying a second decoding associated with an erasure code on each of said decoded blocks of data, defining a second set of blocks of data;
- obtaining useful data from said second set.

In a preferred embodiment, such method for obtaining is remarkable in that said numeral system corresponds to a binary numeral system.

According to an exemplary implementation, the different steps of the method are implemented by a computer software program or programs, this software program comprising software instructions designed to be executed by a data processor of a relay module according to the disclosure and being designed to control the execution of the different steps of this method.

Consequently, an aspect of the disclosure also concerns a program liable to be executed by a computer or by a data processor, this program comprising instructions to command the execution of the steps of a method as mentioned here above.

This program can use any programming language whatsoever and be in the form of a source code, object code or code that is intermediate between source code and object code, such as in a partially compiled form or in any other desirable form.

The disclosure also concerns an information medium readable by a data processor and comprising instructions of a program as mentioned here above.

The information medium can be any entity or device capable of storing the program. For example, the medium can comprise a storage means such as a ROM (which stands for "Read Only Memory"), for example a CD-ROM (which stands for "Compact Disc-Read Only Memory") or a microelectronic circuit ROM or again a magnetic recording means, for example a floppy disk or a hard disk drive.

Furthermore, the information medium may be a transmissible carrier such as an electrical or optical signal that can be conveyed through an electrical or optical cable, by radio or by other means. The program can be especially downloaded into an Internet-type network.

Alternately, the information medium can be an integrated circuit into which the program is incorporated, the circuit being adapted to executing or being used in the execution of the method in question.

According to one embodiment, an embodiment of the disclosure is implemented by means of software and/or hardware components. From this viewpoint, the term "module" can correspond in this document both to a software component and to a hardware component or to a set of hardware and software components.

A software component corresponds to one or more computer programs, one or more sub-programs of a program, or more generally to any element of a program or a software program capable of implementing a function or a set of functions according to what is described here below for the module concerned. One such software component is executed by a data processor of a physical entity (terminal, server, etc.) and is capable of accessing the hardware resources of this physical entity (memories, recording media, communications buses, input/output electronic boards, user interfaces, etc.).

Similarly, a hardware component corresponds to any element of a hardware unit capable of implementing a function or a set of functions according to what is described here below for the module concerned. It may be a programmable hardware component or a component with an integrated circuit for the execution of software, for example an integrated circuit, a smart card, a memory card, an electronic board for executing firmware etc. In a variant, the hardware component comprises a processor that is an integrated circuit such as a central processing unit, and/or a microprocessor, and/or an Application-specific integrated circuit (ASIC), and/or an Application-specific instruction-set processor (ASIP), and/or a graphics processing unit (GPU), and/or a physics processing unit (PPU), and/or a digital signal processor (DSP), and/or an image processor, and/or a coprocessor, and/or a floating-point unit, and/or a network processor, and/or an audio processor, and/or a multi-core processor. Moreover, the hardware component can also comprise a baseband processor (comprising for example memory units, and a firmware) and/or radio electronic circuits (that can comprise antennas) which receive or transmit radio signals. In one embodiment, the hardware component is compliant with one or more standards such as ISO/IEC 18092/ECMA-340, ISO/IEC 21481/ECMA-352, GSMA, StoLPaN, ETSI/SCP (Smart Card Platform), GlobalPlatform (i.e. a secure element). In a variant, the hardware component is a Radio-frequency identification (RFID) tag. In one embodiment, a hardware component comprises circuits that enable Bluetooth communications, and/or Wi-fi communications, and/or Zigbee communications, and/or USB communications and/or Firewire communications and/or NFC (for Near Field) communications.

It should be noted that a step of obtaining an element/value in the present document can be viewed either as a step of reading such element/value in a memory unit of an electronic device or a step of receiving such element/value from another electronic device via communication means.

In a variant, it is proposed an electronic device for storing input data on a set of DNA strands, said input data being represented in a numeral system. This electronic device is remarkable in that it comprises:
  means for formatting said input data into a set of blocks of data, each block of data having a size inferior to a size of one DNA strand;
  means for applying a first encoding with an erasure code on said set of blocks of data, defining a first set of modified blocks of data, each modified block of data having a size inferior to a size of one DNA strand;
  means for applying a second encoding using an error correcting code on each modified block of data of said first set, defining a second set of modified blocks of data, each modified block having a size inferior to a size of one DNA strand;
  means for encoding each modified block of data of said second set into a nucleotides block sequence;
  means for generating a set of DNA strands, each DNA strand comprising a nucleotides block sequence obtained through said encoding.

In a variant, it is proposed an electronic device for obtaining useful data via a set of DNA strands. This electronic device is remarkable in that it comprises:
  means for selecting at random DNA strands belonging to said set of DNA strands;
  means for sequencing said selected DNA strands, delivering a set of nucleotides block sequence;
  means for converting each nucleotides block sequence into a numeral system, each nucleotides block sequence being associated with a corresponding block of data;
  means for applying a first decoding using an error correcting code on each block of data, defining a first set of decoded blocks of data;
  means for applying a second decoding associated with an erasure code on each of said decoded blocks of data, defining a second set of blocks of data;
  means for obtaining useful data from said second set.

BRIEF DESCRIPTION OF THE DRAWINGS

The above and other aspects of the invention will become more apparent by the following detailed description of exemplary embodiments thereof with reference to the attached drawings in which.

DETAILED DESCRIPTION

As mentioned previously, the proposed technique relies on (i) an inner error detecting/correcting code (e.g. LDPC combined with a CRC) that protects against errors from sequencing and synthesis, and (ii) an outer erasure correcting codes (e.g., fountain codes) for accessing the data efficiently in spite of the random access provided by the sequencing process.

Figure 1:
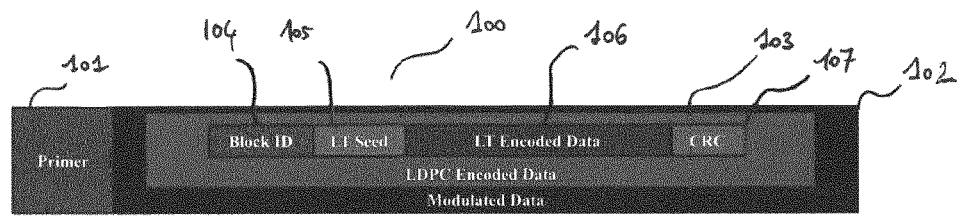
FIG. 1 presents a DNA strand for storing data, according to one embodiment of the invention.

FIG. 1 presents a DNA strand for storing data, according to one embodiment of the invention.

The inner code which aims at ensuring that the outer code, which is a fountain code in one embodiment of the invention, will only have to deal with erasures. Indeed, efficiently decoding a fountain code is possible only for erasures but not for errors (i.e., either we get a correct value, or we don't get a value).

A strand of DNA, depicted in FIG. 1 comprises a short sequence of nucleotides called the primer, referenced 101, and bunch of nucleotides containing the data, referenced 102. The primer 101 is a specific sequence that allows selecting all molecules with a given primer in a solution. This selection relies on the PCRA bio-chemical reaction that ensures that strand with a given primer are copied over and over until the concentration of sequences not starting by the given primer is negligible. It should be noted that, in another embodiment, such strand of DNA can also comprise a primer at the end of the strand (for replicating the "reverse" strand).

The actual data 102 is stored after the primer 101 and consist of modulated data 102. The modulation aims at avoiding specific local patterns such as GGGG that can pose problem for bio-chemical reactions and sequencing. This modulation is a local transformation (every 4 bits are modulated to 3 nucleotides—6 bits). In one embodiment, this modulation can be a local transformation (lookup table, . . . ), or it can be a convolutional code. In one embodiment, the modulated data contains LDPC encoded data, referenced 103. The LDPC encoding aims at protecting against errors and thus helps obtaining "correct" sequences in spite of local sequencing and synthesis errors. The data encoded 103 is (possibly) further protected by a CRC, referenced 107, to ensure that no erroneously decoded sequence is passed to the outer code, as the outer code is unable to deal with errors.

The useful part of the data consists of a block id, and of an encoded data chunk/block together with a seed, referenced 105, describing the encoding applied to the chunk. It should be noted that such seed 105 corresponds to an identifying if the outer erasure correcting code is a deterministic code. In the case that the outer erasure correcting code is a randomized code, the seed 105 is used for generating random numbers, as for example in a Raptor code, or an LT code. This seed and the encoded chunk form one symbol for the outer code (e.g., LT code, LDPC, Reed-Solomon code), referenced 106. All correct symbols (according to the CRC) for a same primer and a same block id are passed to a decoder for the outer code.

Figure 2:
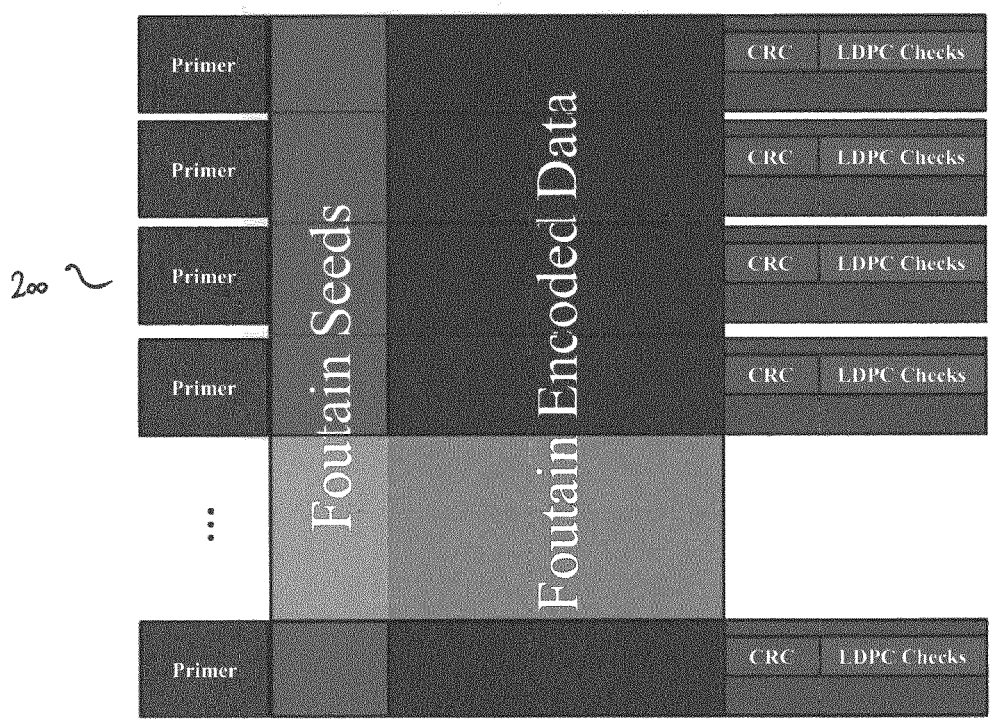
FIG. 2 presents a set of several DNA strands according to one embodiment of the invention, which presents the structure of an outer code.

FIG. 2 presents a set of several DNA strands according to one embodiment of the invention, which presents the structure of an outer code.

The sequencing consists in picking at random strands in a solution containing a very large number of copies of each strand. Hence, a strand may be read several times: it can be considered as random sampling with replacement. With such kind of access to data, getting the last missing symbol when k−1 out of k symbols have already been read requires reading k symbols on average. This problem is known as the coupon's collector problem. Reading all k different symbols requires reading $\Omega(k \log k)$ symbols (i.e., 6,900 reads for 1,000 different symbols, 1,150,000 reads for 100,000 different symbols).

In transmission, the coupon collector's problem is encountered when sending data through a broadcast/multi-cast channel and can be solved relying on fountain codes (e.g., LT codes, raptor codes) or codes with a low rate (e.g., LDPC). Doing so decrease the probability to get a symbol that has already been read and reduce the number of reads needed to read k different symbols (i.e., a number of symbols sufficient for decoding.)

We use a similar scheme for DNA storage and synthesize a higher number strands (each containing one encoded symbols). However, rather than having an infinite number of encoded symbols as with regular fountain codes, we limit the number of symbols we synthesize to account for the fact that DNA synthesis is costly and that synthesis occurs at time t and sequencing occurs at time t+δt with a very large δt. When a DNA strands is sequenced and its inner code decodes successfully, the resulting symbol is passed to the fountain code decoder (outer code) (FIG. 2). When the fountain codes has processed $k(1+\epsilon)$ symbols the initial data is fully recovered with high probability.

Figure 3:
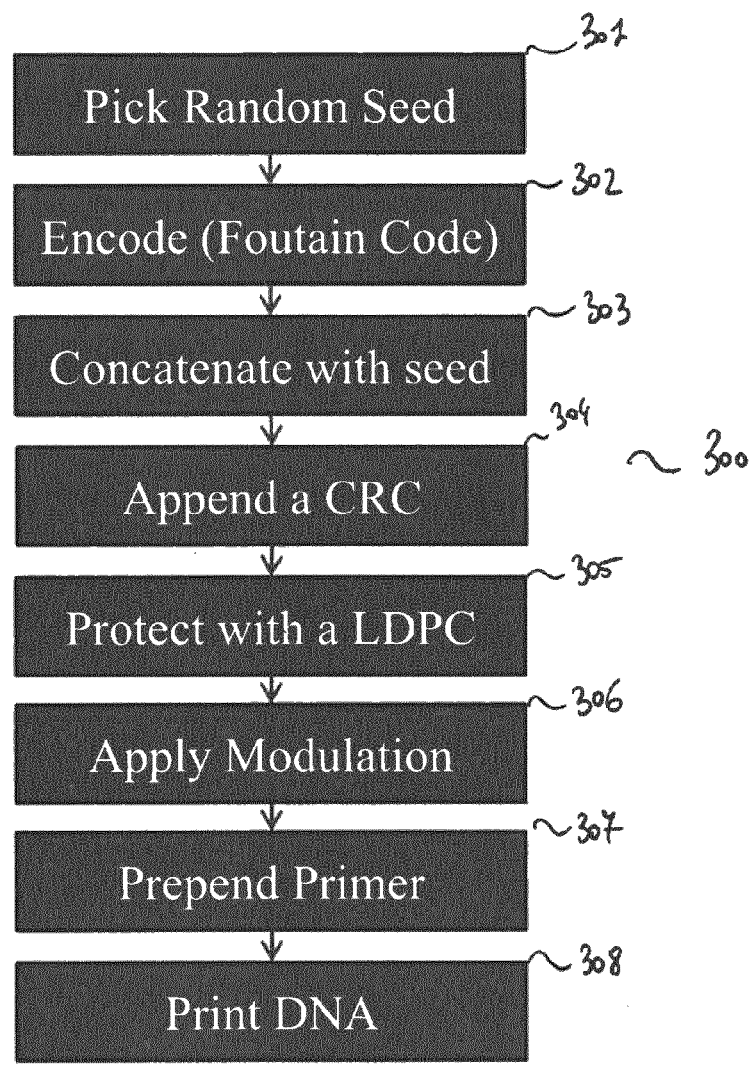
FIG. 3 presents some steps of a method for storing input data on a set of DNA strands according to one embodiment of the invention.

FIG. 3 presents some steps of a method for storing input data on a set of DNA strands according to one embodiment of the invention.

More precisely, such method for storing input data on a set of DNA strands, referenced 300, comprises:

a step referenced 301, of obtaining a random seed that is used to define a fountain seed;

a step referenced 302, of applying a erasure code such as a Fountain code;

a step referenced 303, of concatenating the random seed with the result of the application of the Fountain code in step 302;

a step referenced 304, of determining a CRC;

a step referenced 305, of protecting the output of step 303 and 304 with a LDPC code;

a step referenced 306, of applying a modulation to the obtained data in order to obtain a sequence of nucleotides that is intended to be stored on a DNA strand;

a step referenced 307, of prepending a primer in order to define a set of DNA strand that has a common primer;

a step referenced 308, of printing the primer and the sequence of nucleotides obtained from step 306. It should be noted that step 304 can be optional as mentioned previously.

Figure 4:
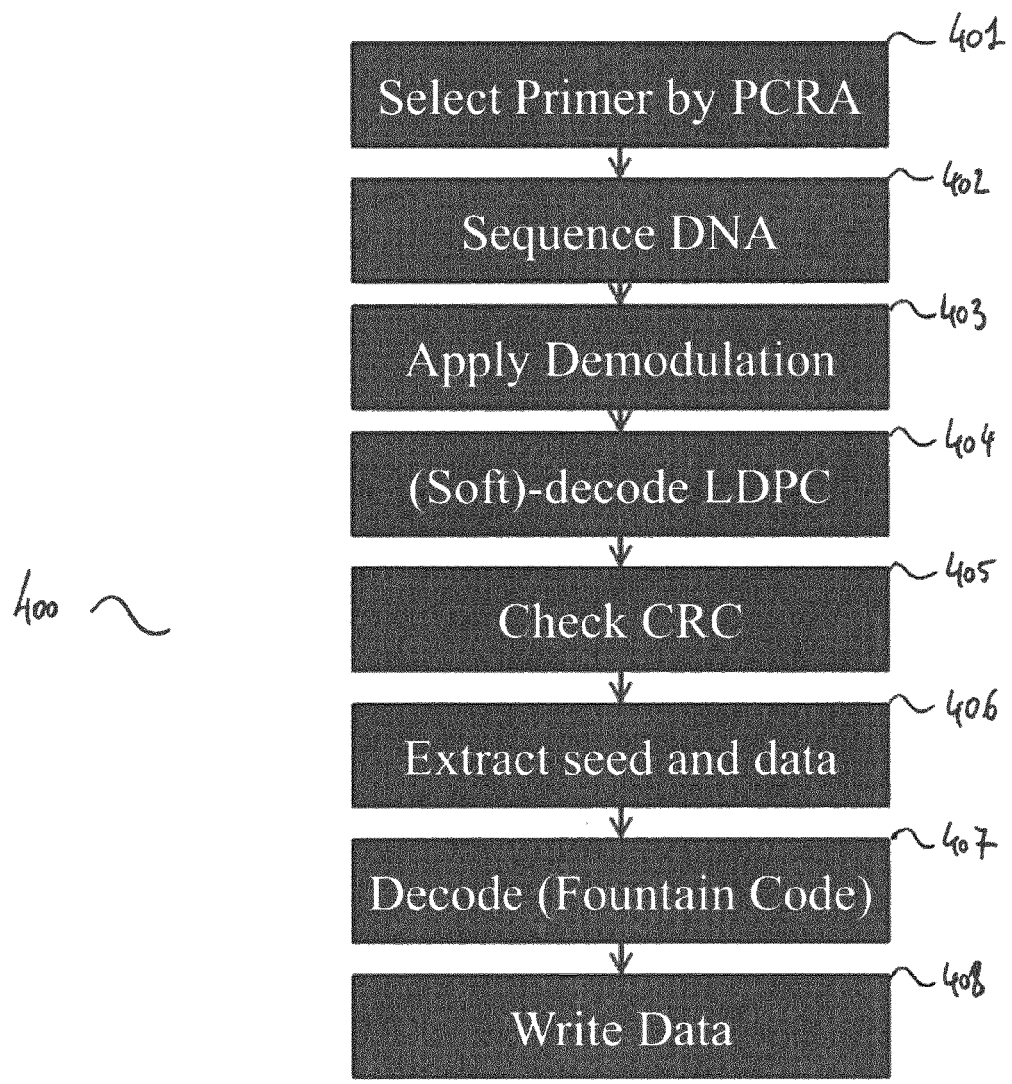
FIG. 4 presents some steps of a method for reading data on a set of DNA strands according to one embodiment of the invention.

FIG. 4 presents some steps of a method for reading data on a set of DNA strands according to one embodiment of the invention.

More precisely, such method for reading data on a set of DNA strands, referenced 400, comprises:

a step referenced 401, of selecting primer by a biological reaction such as PCRA;

a step referenced 402, of sequencing DNA strands chosen randomly in a solution comprising the DA content;

a step referenced 403, of applying a demodulation (e.g. the inverse of the step 306) in order to obtain a digital content from a sequence of DNA comprised in DNA strands;

a step referenced 404, of decoding an LDPC code;

a step referenced 405, of verifying a CRC code;

a step, referenced 406, of extracting seed and data (corresponding to the digital equivalent of the sequences 105 and 106);

a step, referenced 407, of decoding the Fountain code;

a step, referenced 408, of writing the obtained data on a memory of an electronic device.

Figure 5:
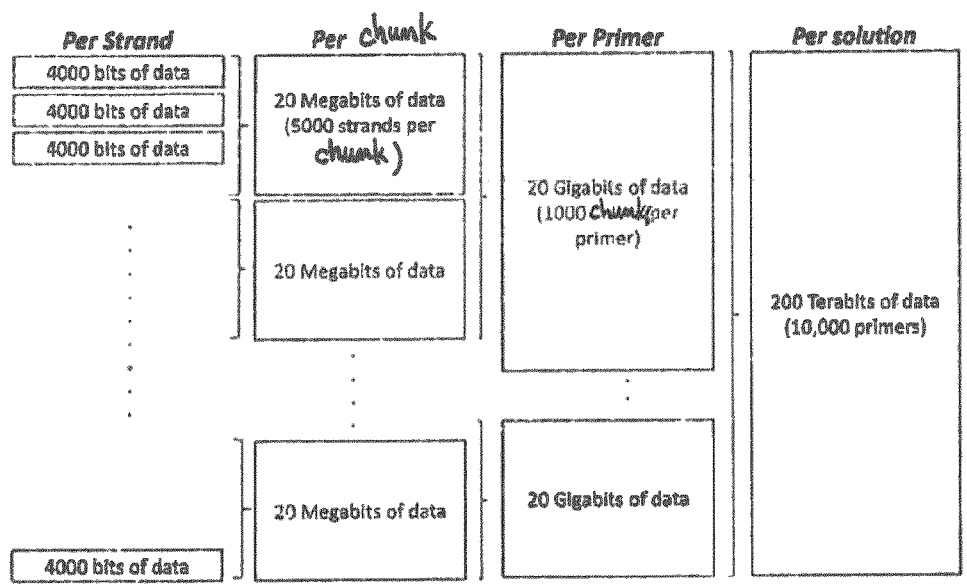
FIG. 5 presents an estimation of the amount of data handled by the proposed technique.

FIG. 5 presents an estimation of the amount of data handled by the proposed technique.

In order to store tera-bytes to peta-bytes of data, it is necessary to split data into chunks that are decoded independently; otherwise the encoding/decoding would become impossible because of the processing and memory requirements. Indeed, assuming strands of length 2,000 bits, practical outer code lengths of 5,000, an efficient modulation (1.5 bits per nucleotide) and a limited overhead of 33% for LDPC, Seed, Block ID and CRC, we can expect to store 20 MB in a single chunk. We need thousands to millions of such chunk to reach a tera or a peta-byte storage capacity.

To deal with such a number of chunks, The proposed technique should gather the chunks by groups of 1000 chunks and assigned a common primer. Each group can be accessed by isolating it (i.e., selecting strands that match the primer) before sequencing it using the biochemical PCRA reaction. If we have 10,000 such groups, we can have 200 terabits of data in the solution. In order to ensure that no single bit is erroneous in this setting (10,000,000 total chunks), the probability of errors for the inner and the outer code must be very low. The overall structure is shown in FIG. 5.

The approach of the present technique of using LDPC with CRC to correct errors instead of using a technique based on consensus has several advantages.

Indeed, in order to correct errors using consensus, a strand must have been sequenced several times. Sequencing a particular strand multiple times given the random access to strands in the solution is inefficient and is not compatible with the fountain-code based approach that we advocate for solving the coupon's collector issue. Furthermore, the combination of the LDPC with CRC has the advantage that each strand can be processed independently from the others thus avoiding the complex sequence-alignment step that requires all sequences to be compared to each other's.

It should also be noted that it is not necessary to leverage the fact that some strands may be read several times during the execution of a method for reading data on a set of DNA strands.

Indeed, even if we could leverage the additional information gathered during several readings of a single strand to perform soft-decoding on the inner-code, and help it correct errors, a strand is unlikely to be undecodable given appropriate LDPC+CRC, and unless the outer code has a rate close to 1 (in which case the access becomes inefficient), it is unlikely that the strand that cannot be decoded is the one that is read a second time. Hence, it is simpler and more efficient to have an appropriate outer code and just drop strands that cannot be decoded.

At last, it should be noted that the synthesis costs is not so deterrent. With a given archival goal, where random access to subset of the data is not needed, some sort of compression should be used (lossless, or lossy with very low distortion) as the main way to reduce the amount of data. This resulting amount of data is the minimal amount of DNA to synthesize, assuming that the synthesis process has no errors and that we can afford as much time as needed for sequencing, is the raw data converted. Once we add redundancy (e.g., erasure correcting codes), we may end up with a 50-100% overhead for the inner code (pessimistic assumption) and a 33-100% overhead for the outer code (could be reduced by accepting a decrease in efficiency). This implies that we have to synthesize 2 to 4 times the minimal amount of data. However, as these error correcting codes are designed to handle the errors, we can accept synthesis processes that lead to more errors. Anyway, the cost of synthesis has to be paid and a lower bound on this cost is the amount of data to store (as compressed as acceptable but without indexes and redundancy). Hence, we cannot enhance much the synthesis except by using efficient redundancy schemes instead of using plain repetition/replication as in Goldman et al.'s approach in document WO2013/178801.

The redundancy level has to be tuned to minimize the cost (according to given synthesis and sequencing error-rate and cost). However, reducing it can only halves the synthesis cost (according to the previous hypothesis) while it can significantly increase the number of sequencing (from one to thousands) needed because of sequencing errors (inefficient inner code) and because of "coverage" issues linked with the coupon-collector issue (inefficient outer code). No redundancy is not an option given that errors may occur at synthesis time and that some sequences to be synthesize may be missing in the final solution (e.g., legally-forbidden, biologically-instable patterns): A too low redundancy may render the file unrecoverable if too much strands are missing, incorrectly synthesized, or damaged early in PCRA.

Hence, the best remaining option would be to rely on cheaper yet less reliable synthesis processes and tolerate synthesis errors thanks to the redundancy introduced by inner and outer codes.

Figure 6:
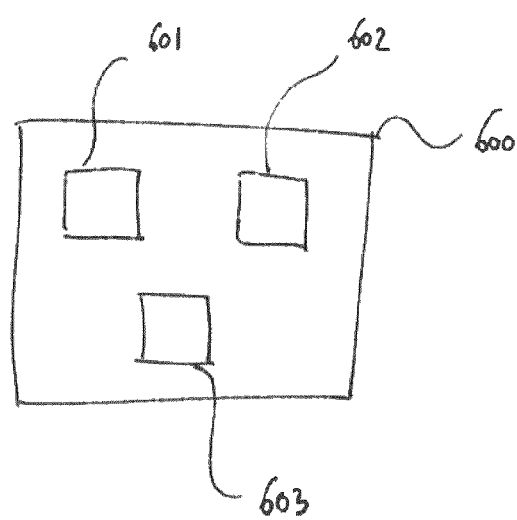
FIG. 6 presents a device that can be used to perform one or several steps of methods disclosed in the present document.

FIG. 6 presents a device that can be used to perform one or several steps of methods disclosed in the present document. Such device, referenced 600 comprises a computing unit (for example a CPU, for "Central Processing Unit"), referenced 601, and one or more memory units (for example a RAM, (for "Random Access Memory") block in which intermediate results can be stored temporarily during the execution of instructions a computer program, or a ROM block in which, among other things, computer programs are stored, or an EEPROM ("Electrically-Erasable Programmable Read-Only Memory") block, or a flash block) referenced 602). Computer programs are made of instructions that can be executed by the computing unit. Such device 600 can also comprise a dedicated unit, referenced 603, constituting an input-output interface to allow the device 600 to communicate with other devices. In particular, this dedicated unit 603 can be connected with an antenna (in order to perform communication without contacts), or with serial ports (to carry communications "contact").

In an alternative embodiment, some or all of the steps of the method previously described, can be implemented in hardware in a programmable FPGA ("Field Programmable Gate Array") component or ASIC ("Application-Specific Integrated Circuit") component.

In an alternative embodiment, some or all of the steps of the method previously described, can be executed on an electronic device comprising memory units and processing units as the one disclosed in the FIG. 6.

Such device 600 can be used in combination with a DNA sequencer and/or with a DNA laser printer (as proposed by the company Cambrian Genomics) or devices of that kind, that have common objectives. Indeed, such DNA laser printer comprises means for encoding each modified block of data of said second set into a nucleotides block sequence, and/or means for generating a set of DNA strands, as mentioned previously. Moreover, a DNA sequencer comprises means for selecting at random DNA strands belonging to said set of DNA strands, and/or means for sequencing said selected DNA strands, delivering a set of nucleotides block sequence, as mentioned previously.

The invention claimed is:

1. A method for storing input data on a set of DNA strands, said input data being represented in a numeral system, wherein the method comprises:
   formatting said input data into a set of blocks of data, each block of data having a size inferior to a size of one DNA strand;
   applying a first encoding with an erasure code involving all the blocks of said set of blocks of data, defining a first set of modified blocks of data, each modified block of data having a size inferior to a size of one DNA strand;
   concatenating a seed associated with said erasure code to each modified block of data of said first set, delivering a second set of modified blocks of data, each modified block of data having a size inferior to a size of on DNA strand;
   applying a second encoding using an error correcting code on each modified block of data of said second set, defining a third set of modified blocks of data, each modified block having a size inferior to a size of one DNA strand;
   encoding each modified block of data of said third set into a nucleotides block sequence;
   generating a set of DNA strands, each DNA strand comprising a nucleotides block sequence obtained through said encoding.

2. The method for storing according to claim 1, wherein said generating uses a synthesis process.

3. The method for storing according to claim 1, wherein said input data corresponds to data that has been obtained via a compression process.

4. The method for storing according to claim 1, wherein said method further comprises replicating at least one strand that belongs to said set of DNA strands.

5. The method for storing according to claim 1, wherein said numeral system corresponds to a binary numeral system.

6. The method for storing according to claim 1, wherein said encoding uses a look-up table that put into correspondence a sequence of elements of said numeral system into a sequence of nucleotides.

7. The method for storing according to claim 1, wherein said encoding uses a modulation code or a convolutional code.

8. The method for storing according to claim 1, wherein it further comprises replicating DNA strands belonging to said generated set of DNA strands via a biochemical reaction.

9. The method for storing according to claim 1, wherein said erasure code belongs to a group comprising:
    a fountain code;
    a tornado code;
    a low-density parity-check code;
    a Reed-Solomon code;
    a maximum distance separable code.

10. The method for storing according to claim 1, wherein said error correcting code belongs to a group comprising:
    a low-density parity-check code;
    a Reed-Solomon code.

11. The method for storing according to claim 1, wherein it further comprises applying a cyclic redundancy check code either on said first set or on said second set or on said third set.

12. The method for storing according to claim 1, wherein said generating a set of DNA strands further comprises inserting a common primer on said generated DNA strands.

13. A method for obtaining useful data via a set of DNA strands, wherein the method comprises:
    selecting at random DNA strands belonging to said set of DNA strands;
    sequencing said selected DNA strands, delivering a set of nucleotides block sequence;
    converting each nucleotides block sequence into a numeral system, each nucleotides block sequence being associated with a corresponding block of data;
    applying a first decoding using an error correcting code on each block of data, defining a first set of decoded blocks of data;
    applying a second decoding associated with an erasure code involving all the decoded blocks of data, defining a second set of blocks of data, wherein each decoded block comprises a seed being associated with said erasure code;
    obtaining useful data from said second set.

14. The method for obtaining according to claim 13, wherein numeral system corresponds to a binary numeral system.

15. An electronic device for storing input data on a set of DNA strands, said input data being represented in a numeral system, wherein the electronic device comprises:
    means for formatting said input data into a set of blocks of data, each block of data having a size inferior to a size of one DNA strand;
    means for applying a first encoding with an erasure code involving all the blocks of said set of blocks of data, defining a first set of modified blocks of data, each modified block of data having a size inferior to a size of one DNA strand;
    means for concatenating a seed associated with said erasure code to each modified block of data of said first set, delivering a second set of modified blocks of data, each modified block of data having a size inferior to a size of one DNA strand;
    means for applying a second encoding using an error correcting code on each modified block of data of said second set, defining a third set of modified blocks of data, each modified block having a size inferior to a size of one DNA strand;
    means for encoding each modified block of data of said third set into a nucleotides block sequence;
    means for generating a set of DNA strands, each DNA strand comprising a nucleotides block sequence obtained through said encoding.

16. An electronic device for obtaining useful data via a set of DNA strands, wherein the electronic device comprises:
    means for selecting at random DNA strands belonging to said set of DNA strands;
    means for sequencing said selected DNA strands, delivering a set of nucleotides block sequence;
    means for converting each nucleotides block sequence into a numeral system, each nucleotides block sequence being associated with a corresponding block of data;
    means for applying a first decoding using an error correcting code on each block of data, defining a first set of decoded blocks of data;
    means for applying a second decoding associated with an erasure code involving all the decoded blocks of data, defining a second set of blocks of data, wherein each decoded block comprises a seed being associated with said erasure code;
    means for obtaining useful data from said second set.

* * * * *